(12) United States Patent
Faccioli et al.

(10) Patent No.: US 10,799,279 B2
(45) Date of Patent: Oct. 13, 2020

(54) HANDLE TO APPLY A TORQUE AND DELIVERY UNIT PROVIDED WITH SUCH HANDLE

(71) Applicant: TECRES S.p.A., Sommacampagna (Verona) (IT)

(72) Inventors: Giovanni Faccioli, Monzambano (IT); Renzo Soffiatti, Nogara (IT)

(73) Assignee: TECRES S.P.A., Sommacampagna (VR) (IT)

( * ) Notice: Subject to any disclaimer, the term of this patent is extended or adjusted under 35 U.S.C. 154(b) by 100 days.

(21) Appl. No.: 15/505,368

(22) PCT Filed: Jun. 30, 2015

(86) PCT No.: PCT/IB2015/054920
§ 371 (c)(1),
(2) Date: Feb. 21, 2017

(87) PCT Pub. No.: WO2016/027176
PCT Pub. Date: Feb. 25, 2016

(65) Prior Publication Data
US 2017/0265921 A1      Sep. 21, 2017

(30) Foreign Application Priority Data

Aug. 20, 2014   (IT) .............................. VR2014A0213

(51) Int. Cl.
*A61B 17/88*      (2006.01)
*F16D 7/04*       (2006.01)
(Continued)

(52) U.S. Cl.
CPC ...... *A61B 17/8822* (2013.01); *A61B 17/8811* (2013.01); *A61B 17/8819* (2013.01);
(Continued)

(58) Field of Classification Search
CPC ............ A61B 17/8822; A61B 17/8802; A61B 17/8833; A61B 17/8819; A61B 17/8811;
(Continued)

(56) References Cited

U.S. PATENT DOCUMENTS 4,534,234 A * 8/1985 Cosenza ............... H05K 7/1412
439/347
4,766,641 A * 8/1988 Daglow .................... A47L 5/30
15/390
(Continued)

FOREIGN PATENT DOCUMENTS

DE         1110580      7/1961
DE       102013200741   7/2014
(Continued)

*Primary Examiner* — Amy R Sipp
(74) *Attorney, Agent, or Firm* — Tutunjian & Bitetto, P.C.

(57) ABSTRACT

A handle connectable to a screw-type mechanical drive component for transmitting to the latter a first torque comprises first connection means, defining a constraint axis, for the connection of the handle to the mechanical drive component, a ring nut to which a second torque is manually applicable, support means of the ring nut for rotatably supporting the latter around an axis of rotation coinciding, in use, with the constraint axis, second means for connecting the ring nut to the support means, for connecting/disconnecting the ring nut and the support means in a mechanical and selective way, so that the ring nut is kinematically connected to the support means when rotated around the axis of rotation with a second torque lower than a threshold value and kinematically disconnected from the same upon exceeding such a threshold value.

14 Claims, 3 Drawing Sheets

(51) Int. Cl.
*A61B 90/00* (2016.01)
*A61B 17/00* (2006.01)

(52) U.S. Cl.
CPC .......... *A61B 17/8827* (2013.01); *F16D 7/048* (2013.01); *A61B 2017/00477* (2013.01); *A61B 2090/031* (2016.02); *A61B 2090/032* (2016.02)

(58) Field of Classification Search
CPC .... A61B 17/8825; F16B 31/027; F16B 31/02; B25B 23/141; B25B 23/142; B25B 23/1427; B23B 31/086; B23B 31/38; B23Q 11/04; F16D 7/048; F16D 43/2028
USPC ........................ 411/6, 7; 81/473–476; 464/37
See application file for complete search history.

(56) References Cited

U.S. PATENT DOCUMENTS

| | | | |
|---|---|---|---|
| 5,000,721 A | 3/1991 | Williams | |
| 6,220,415 B1* | 4/2001 | Cosenza | F16D 43/20 192/56.1 |
| 2005/0070915 A1 | 3/2005 | Mazzuca et al. | |
| 2005/0124418 A1 | 6/2005 | McCoy et al. | |
| 2006/0260440 A1 | 11/2006 | Abdelgany | |
| 2006/0264967 A1* | 11/2006 | Ferreyro | A61B 17/00234 606/93 |
| 2009/0133980 A1 | 5/2009 | Swaim et al. | |
| 2010/0275744 A1 | 11/2010 | Wengreen et al. | |
| 2013/0079786 A1* | 3/2013 | Bonnin | A61B 17/8822 606/94 |
| 2014/0123819 A1 | 5/2014 | Beemer et al. | |

FOREIGN PATENT DOCUMENTS

| | | |
|---|---|---|
| DE | 1020113200741 | 7/2014 |
| EP | 2085042 | 8/2009 |

* cited by examiner

HANDLE TO APPLY A TORQUE AND DELIVERY UNIT PROVIDED WITH SUCH HANDLE

TECHNICAL FIELD OF THE INVENTION

The present invention concerns a handle connectable to a mechanical drive component, of the type comprising a screw mechanism, for manually applying a drive torque to the same.

In particular, the present invention concerns a handle through which it is possible to control the maximum drive torque that can be transmitted to such a mechanical drive component.

The present invention also concerns a unit for delivering a fluid, if so desired a liquid or a mixture, comprising a screw mechanism able to be manually drivable in rotation through such a handle.

STATE OF THE ART

Devices for delivering a fluid, if so desired a liquid or a mixture, are known preferably comprising at least one container defining a chamber in which the fluid to be delivered is contained.

The delivery takes place through the thrusting action of a piston, slidably engaged in a sealed manner inside the chamber, which acts on the liquid to be delivered.

The translation of the piston along the chamber is driven by a drive member, preferably comprising a screw mechanism set in rotation through suitable motor means.

The motor means can be of the manually or electromechanically actuated type.

In the first case the motor means comprise a handle operatively connected to the screw mechanism, at the opposite end to that which acting in thrust on the piston.

In practice, by manually rotating the handle the screw mechanism is driven into roto-translation and, consequently, the piston translates thrusting against the fluid contained in the chamber, thus causing its delivery.

Such delivery devices are used in various fields, including that of medicine.

A device for delivering viscous material is disclosed in U.S. 2005/0070915 A1.

With reference to the field of medicine, such delivery devices are generally used to deliver a liquid or a mixture to be injected into the body of a patient.

Advantageously, such delivery devices overall have a simple structure and are easy to use.

However, such delivery devices do not allow precise and effective control of the delivery of the liquid or of the mixture, with particular reference to the pressure with which the delivery takes place.

In greater detail it should be observed that the delivery conditions of the fluid, including the speed and pressure of delivery, vary as a function of the speed and torque with which the operator acts on the handle.

So, in general an operator is unable to ensure continuous and uniform actuation of the screw mechanism, since he/she can make the handle carry out rotation only of limited range.

Quite probably, an operator resuming the rotation of the handle, after having released it possibly can, unintentionally, apply a drive torque that can be greater than that applied during the previous rotation of the handle, also due to the resistance applied by the liquid or by the mixture.

With reference to what is described above, it is clear that such discontinuity in the driving of the screw mechanism has a negative impact upon the delivery conditions of the fluid.

This represents a drawback and a potential danger, particularly in the case in which the fluid to be delivered must be injected inside a human body, since it is not possible to control and limit the pressure and speed of delivery of the fluid.

In the case in which the fluid to be delivered is bone cement, the possibility of controlling the pressure that is exerted on the fluid itself is extremely important.

As known, indeed, bone cement has a viscosity that rapidly increases in a short time period, for example a few minutes.

Generally, in order to counteract the delivery resistance of the bone cement, due to its increase in viscosity, an operator increases the force exerted on the handle, thus applying a greater thrusting force on the piston.

Inside the chamber in which the fluid to be delivered is contained a high pressure is thus reached, even of the order of a hundred bars, with a minimal rotation of the handle for driving the delivery device.

Such a pressure can cause the structural collapse of the delivery device with the consequent bursting thereof and the release of fragments into the surrounding environment.

This is very dangerous, since fragments of the delivery device can be projected into the surgical theatre.

In order to increase the performance of delivery devices of the aforementioned type, means for controlling the delivery pressure, of the mechanical or electromechanical type, have been implemented. For example, it is possible to apply regulating or venting valves to the outlet of the delivery channel of the device, in order to limit the pressure and/or the speed of delivery of the fluid itself.

However, such regulating valves substantially complicate the overall structure of the delivery device.

Moreover, such valves, being arranged downstream of the chamber in which the fluid to be delivered is contained, do not allow possible bursting of the chamber itself to be avoided in the case in which the fluid to be delivered obstructs the outlet channel. In order to further optimise the performance of such delivery devices, in reference to the drawbacks described above, electromechanically controlled drive means within manual driving means have been developed.

In practice, electromechanically controlled drive means comprise electromechanical drive means operatively connected to the screw mechanism of the delivery device.

The driving of the electromechanical drive means is controlled through sensors suitable for managing and controlling the constant operating conditions, with particular reference to the drive torque transmitted.

In practice, the electromechanical drive means allow the operating conditions of the delivery device itself to be controlled effectively.

Such electromechanically controlled delivery devices, whilst proving effective, have a very complex structure and a substantially higher procurement and maintenance cost with respect to that of manually driven delivery devices. This, indeed, limits their use.

U.S. 2010/0275744 A1, EP 2085042 A1, U.S. 2006/0260440 A1 and DE 1110580 B discloses torque limiter devices configured to transfer a torque applied by an user acting on the device and to limit the maximum value of torque transferable by the device itself.

Therefore, there is a need to improve the efficiency of manually driven delivery devices currently available on the market.

SUMMARY OF THE INVENTION

The technical task of the present invention is to improve the state of the art.

In such a technical task, a purpose of the present invention is to provide a handle through which to transmit a drive torque to a mechanical drive component connectable thereto, through first connection means, which makes it possible to control, in an effective and precise manner, the value of the maximum torque that can be transmitted to the component itself.

Another purpose of the present invention is to provide a handle suitable for controlling the maximum torque that can be transmitted through the same, that is easy to use, according to a constructively simple solution.

A further purpose of the present invention is to provide a handle that is easy to implement in fluid delivery devices, comprising delivery means equipped with a screw mechanism, replacing a control handle previously connected to the screw mechanism, in order to increase the efficiency of use of the delivery device itself.

According to an aspect of the present invention, a handle that is connectable to a mechanical drive component to manually apply to the latter a drive torque, according to the present specification, is provided.

According to another aspect of the present invention a delivery unit comprising a handle according to the present specification is provided.

According to a further aspect of the present invention a delivery device is provided comprising a delivery unit according to the present specification.

The present application refers to preferred and advantageous embodiments of the invention.

BRIEF DESCRIPTION OF THE DRAWINGS

Further characteristics and advantages of the present invention will become clearer from the detailed description of a preferred, but not exclusive embodiment, of a handle through which driving a screw mechanism, illustrated for indicating but not limiting purposes in the attached tables of drawings, in which.

DETAILED DESCRIPTION OF THE INVENTION

With reference to the attached figures, a handle for manually applying a drive torque to a mechanical drive component, connectable thereto, is wholly indicated with reference numeral 1.

Preferably, the handle 1 according to the present invention is foreseen, in use, to be connected to a screw mechanism of a mechanical drive component of a delivery device of a fluid, if so desired a liquid or a mixture.

Concerning this, the handle 1 comprises connection means to the screw mechanism, of the removable type.

In the following description reference will be made to a delivery device for medical use, like for example a device suitable for delivering bone cement. However, the scope of protection of the present invention comprises further types of delivery devices used in different fields to medicine, without any limitation.

Preferably, the handle 1 according to the present invention is foreseen to be connected, in use, to a screw-type mechanical drive component 35.

Concerning this, the handle 1 comprises first means 3 for the removable connection of the handle 1 to the screw mechanism 35, defining a constraint axis 2.

According to an aspect of the present invention, as better disclosed hereafter, an operator acting on the handle 1 is able to manually transmit a torque to the mechanical drive component connected to the handle 1 itself through the aforementioned first connection means 3.

As an example, the handle 1 according to the present invention can be connected to a mechanical drive component of a delivery unit, for controlling the driving in translation of a piston slidable in a seal manner inside a chamber.

The piston acts by thrusting on a fluid thus causing the delivery of the latter from the device.

A delivery unit comprising the aforementioned handle 1 also form an object of the present invention.

Preferably, with reference to what is illustrated in the attached FIGS. 1-4 and 6, the handle 1 is substantially discoidal shaped.

However, further configurations of the handle 1, not illustrated in the attached figures, are possible, in which the handle 1 itself has a cylindrical shape, for example similar to a knob, or in general a shape the facilitates its gripping and actuation by a user.

The handle 1 is suitable for controlling the threshold value of a drive torque that can be transmitted to the drive member connected thereto.

According to this, it should be observed that the handle 1 according to the present invention comprises a ring nut 4, to which it is possible to apply a torque to be transmitted to a mechanical drive component, comprising a screw mechanism, to which the handle 1 can be connected.

Concerning this, the handle 1 comprises support means 5 of the ring nut 4, connectable to a mechanical drive component through the first connection means 3 and suitable for supporting the ring nut 4 rotatably about an axis of rotation 6.

The handle 1 also comprises second means 7 for the connection of the ring nut 4 to the support means 5.

It should be observed that the support means 5 are configured so as to make the axis of rotation 6 of the ring nut 4 coincide, in use, with the constraint axis 2 of the first connection means 3.

The first connection means 3 preferably comprise a seat 44 centrally provided in the support means 5, equipped with a through opening 45 through which a screw or a similar element for the connection of the handle 1 to an end of the screw mechanism is housed.

In greater detail, the seat 44 in use lies along the axis of rotation 6.

Due to the internal friction in the handle 1, although low, the torque transmitted to the mechanical drive component connected to the handle 1 could be slightly less than the torque applied to the ring nut 4.

Therefore, the torque transmitted to the component connected to the handle 1 will hereafter be indicated as first torque, to distinguish it from the second torque applied to the ring nut 4.

In practice, the second torque applied to the ring nut 4 acts in antagonism to a resistant torque acting on the first connection means 3.

The second connection means 7 are for connecting/disconnecting the ring nut 4 and the support means 5 to one another in a mechanical and selective manner, so that the ring nut 4 is kinematically connected to the support means 5 when rotated according to at least one direction of rotation, about the axis of rotation 6, with a second torque lower than a predetermined threshold value and kinematically disconnected from them once such a threshold value is exceeded, as described more clearly hereafter.

The ring nut 4 has an internal surface 8, an external surface 9, separated from one another, and lateral surfaces 10, opposite one another, for connecting the internal surface 8 and the external surface 9.

According to a version of the present invention, the ring nut 4 comprises along the external surface 9 at least one gripping element 11.

The gripping element 11 projects from the external surface 9 and is shaped so as to promote the rotational actuation of the ring nut 4 about the axis of rotation 6.

As an example, the gripping element 11 is shaped like a protuberance or a ridge or an elongated element or an arm or similar.

The support means 5 are substantially spool shaped and comprise a first end portion 12, a second end portion 13 connected together through removable connection means 14.

As an example, the connection means 14 can be of the snap type, comprising tongues or similar that project from the first end portion 12 and can be engaged in respective seats formed in the second end portion 13 or vice-versa.

According to further versions of the present invention, not illustrated in the attached figures, the connection means 14 can comprise screw-type elements able to engage in respective seats formed in the first end portion 12 or in the second end portion 13 or bolts or equivalent means.

The first end portion 12 and the second end portion 13 have a substantially cylindrical or discoidal configuration.

In use, the support means 5 are operatively connected to the ring nut 4 so that one from the first end portion 12 and/or the second end portion 13 is laterally engaged in abutment in a respective seat 15 made along the lateral surfaces 10 of the ring nut 4.

The seat 15 has a substantially annular shape, and is made at least near to the internal surface 8.

In practice, the ring nut 4 and the support means 5 are operatively associated with each other so as to be able to mutually rotate about a common axis of rotation, which in use corresponds to the axis of rotation 6.

As can easily be foreseen, when the handle 1 is connected to a component of a screw mechanism, the aforementioned axis of rotation 6 coincides with the axis of rotation of the aforementioned screw mechanism.

The second connection means 7 comprise at least one elastic element 16 and engagement means 17, suitable for selectively engaging the at least one elastic element 16.

The engagement between the at least one elastic element 16 and the engagement means 17 occurs through a substantial shape coupling as better described hereafter.

In practice, the at least one elastic element 16 is such as to remain connected to the engagement means 17 when the torque that the second transmission means 7 must transfer to the mechanical drive component is below a predetermined threshold value.

When the torque to be transmitted is above such a threshold value, the at least one elastic element 16 starts to slide with respect to the engagement means 17, thus kinematically disconnecting therefrom.

In use, the at least one elastic element 16 and the relative engagement means 17 are arranged between the ring nut 4 and the support means 5.

The at least one elastic element 16 comprises a base portion 18 from which at least one appendage 19 extends equipped with a free end 20.

The appendage 19, which substantially acts as a spring, extends from the base portion 18 for a portion such as to allow the free end 20 to be placed in abutment against the engagement means 17.

Figure 1:
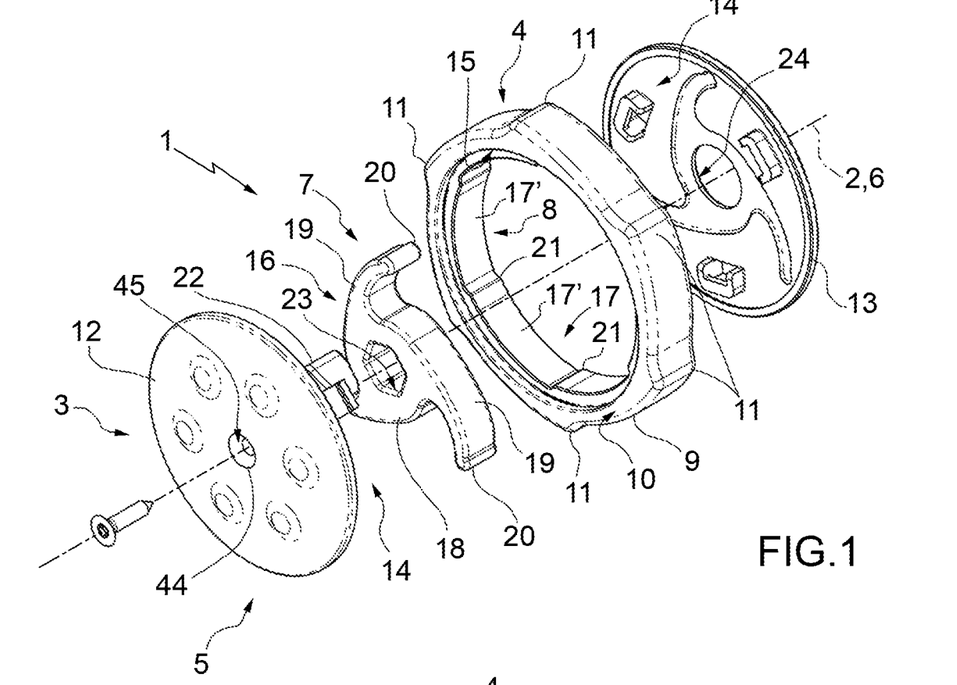
FIG. 1 is an exploded perspective view of a handle according to the present invention.
Figure 2:
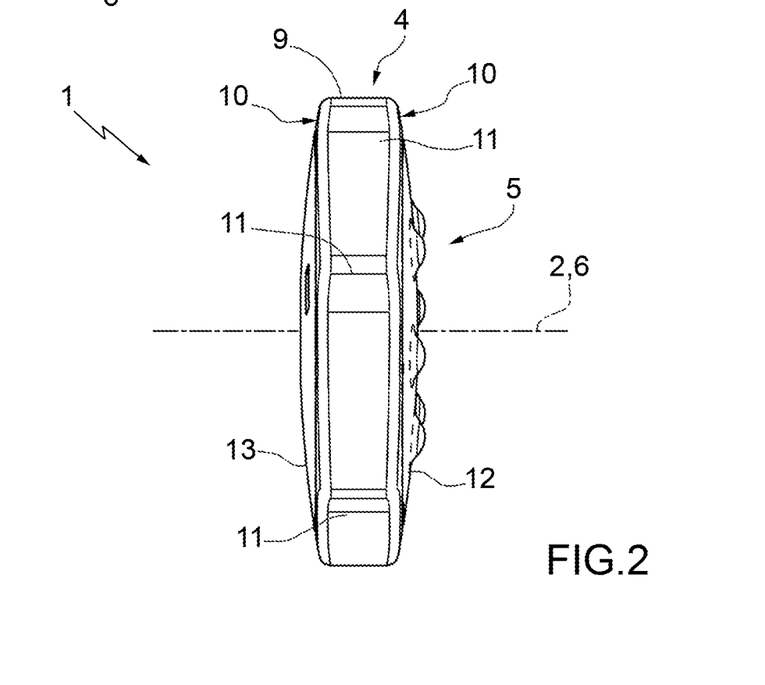
FIG. 2 is a side view of the handle according to FIG. 1.
Figure 3:
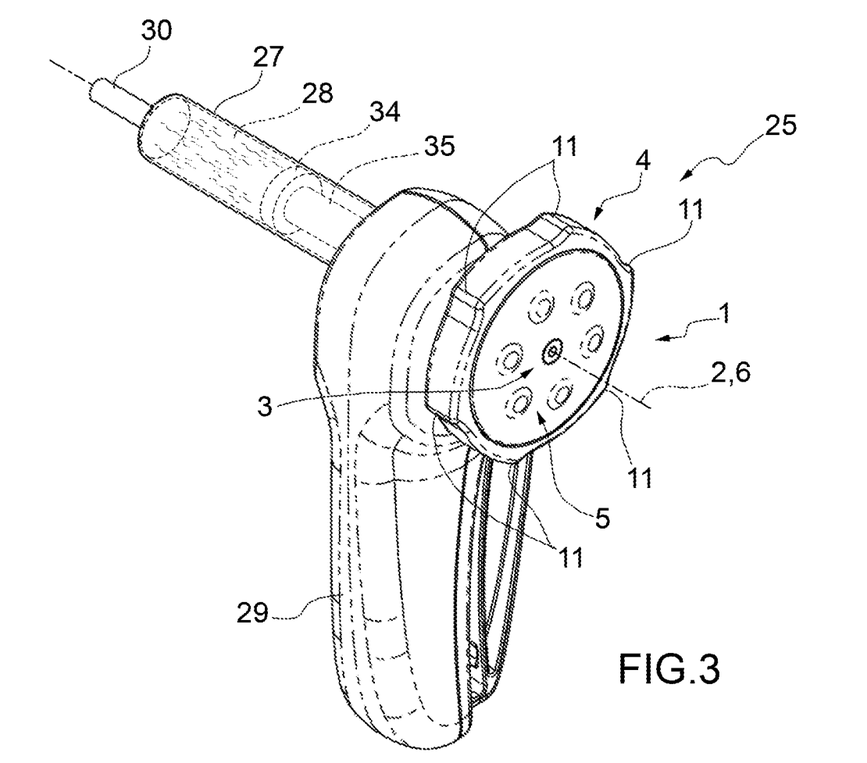
FIG. 3 is a perspective view from above of a delivery unit comprising a handle according to FIG. 1.
Figure 4:
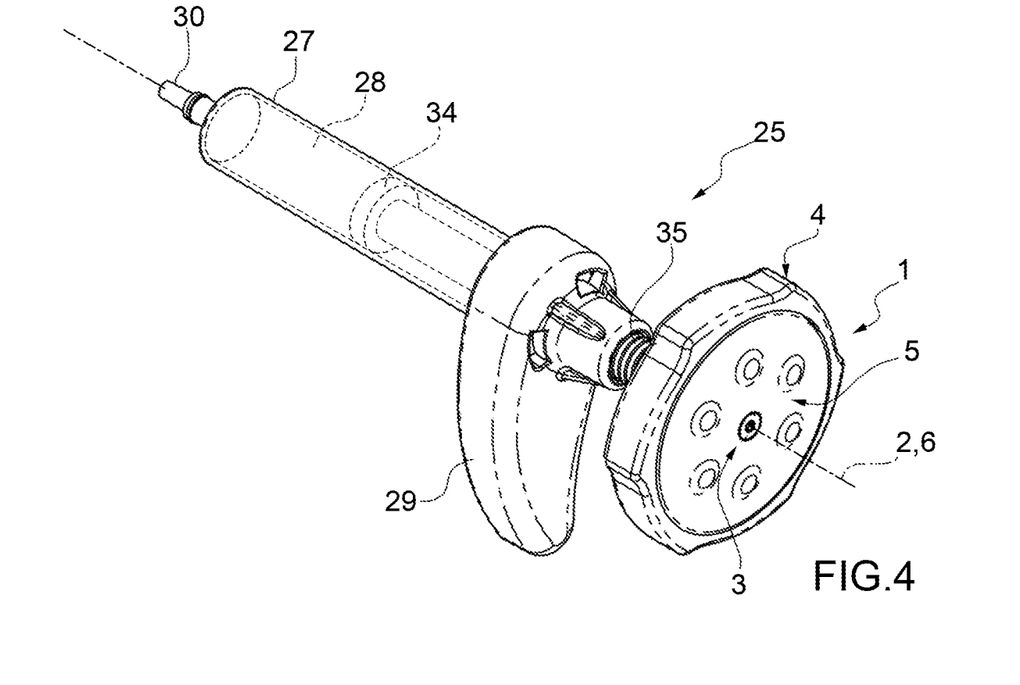
FIG. 4 is a perspective view from above of some components of the delivery unit according to FIG. 3.

According to a version of the present invention, illustrated in FIG. 1, the at least one appendage 19 is shaped like a substantially curved blade.

The at least one appendage 19 can be shaped differently, for example as a rod-shaped element or a tongue or in general like an elongated element suitable for extending from the base portion 18 towards the engagement means 17.

In the version illustrated in FIG. 1 the at least one elastic element 16 comprises three appendages 19 equally spaced apart and with the same direction of inclination.

Further shapes of the at least one elastic element 16 are possible, comprising a greater or smaller number of appendages 19, in any case oriented with the same direction of inclination and, preferably, positioned equally spaced apart without for this reason departing from the scope of protection of the present invention.

According to an aspect of the present invention, the at least one appendage 19 is preferably tapered from the base portion 18 from which it projects.

Advantageously, the at least one appendage 19 is thus shaped so as to act as a spring characterised by a variable rigidity as a function of the direction along which the spring itself is deformed.

The engagement means 17 comprise at least one protuberance 21 suitable for intercepting an end 20 of the at least one elastic element 16, during use.

Preferably, the engagement means 17 comprise a plurality of protuberances 21.

According to a version of the present invention, the at least one elastic element 16 is connected to the support means 5, and the protuberances 21 are made along the internal surface 8 of the ring nut 4, preferably equally spaced apart.

According to further version of the present invention, not illustrated in the attached figures, the at least one elastic element 16 is connected inside the ring nut 4, and the protuberances 21 are provided along the support means 5, in a position arranged between the first end portion 12 and the second end portion 13, equally spaced apart.

The at least one elastic element 16 can be removably connected to the support means 5.

Concerning this, the support means 5 usefully comprise constraint means 22 suitable for preventing a relative rotation between the at least one elastic element 16 and the support means 5.

With reference to the embodiment illustrated in FIG. 1, the constraint means comprise a pin 22 that extends from the first end portion 12 and is received in a corresponding seat 24 obtained in the second end portion 13.

According to further version that is not illustrated in the figures, the position of the pin 22 and of the seat 24 can be inverted with each other.

In use, the pin 22 is foreseen to be engaged in a respective through opening 23 obtained in the at least one elastic element 16, through a shape coupling.

According to an aspect of the present invention, the second connection means 7 are for kinematically connecting/disconnecting the ring nut 4 to/from the support means 5, in a mechanical manner, as a function of the value of the second drive torque applied to the ring nut 4 with respect to a predetermined threshold value.

Therefore, between the ring nut 4 and the support means 5 there can temporarily be a relative sliding at the moment when the second torque applied to the ring nut 4 is greater than a predetermined threshold value. In practice, in such a condition of use, the ring nut 4 rotates idly with respect to the support means 5, about the axis of rotation 6, thus not being able to transmit any torque to the support means 5.

Consequently, the handle 1 does not transmit ay first torque to the mechanical drive component to which it is constrained through the first connection means 3.

As soon as the value of the second torque applied to the ring nut 4 falls within a predetermined range of values, the second connection means 7 restore the kinematic connection between the ring nut 4 and the support means 5, constraining them to each other again.

Advantageously, the maximum value of the first torque that can be transmitted through the handle 1 according to the present invention is limited to a predetermined threshold value, in a solution that is efficient, extremely simple and free from malfunction such as jamming or sticking.

Continuing what has been described earlier, relative to the characteristics of the at least one elastic element 16, the at least one appendage 19 is shaped so as to be deformable when the ring nut 4 is rotated about the axis of rotation 6.

The deformation of the at least one elastic element 16 occurs through the effect of the action of a protuberance 21 that pushes on the at least one appendage 19.

The protuberance 21 in use pushes on the free end 20, until the at least one appendage 19 is deformed until disengaging it from the protuberance 21 itself.

In this way, the kinematic connection between the at least one elastic element 16 and the ring nut 4, and therefore between the support means 5 and the ring nut 4 is interrupted.

By acting with a rotation in the opposite direction, on the other hand, the at least one appendage 19 is substantially undeformable, thus maintaining the connection between the ring nut 4 and the support means 5.

According to further version of the present invention, the engagement means 17 can have connecting ramps 17' between one protuberance 21 and the next.

As an example, with reference to the embodiment illustrated in FIG. 1, the ramps 17' are arranged along the internal surface 8 of the ring nut 4. The ramps 17' act as a wedging element for the free end 20 of the at least one appendage 19.

In fact, the free end 20, being wedged against the ramps 17' of the engagement means 17, constrains the ring nut 4 to the support means 5.

As can be foreseen, the wedging between the free end 20 and at least one ramp 17' is obtained by rotating the ring nut 4 with respect to the support means 5 with a predetermined direction of rotation.

In order to be able to release the ring nut 4 from the support means 5 it is sufficient to rotate the ring nut in the opposite direction.

As can be foreseen, the direction with which it is necessary to actuate the ring nut 4 in rotation about the axis 6, to transmit a first torque to a screw mechanism connected to the handle 1 itself, is the same as the predetermined driving direction of the screw mechanism.

The kinematic engagement/disengagement between the ring nut 4 and the support means 5 is controlled through the second transmission means 7, in a quick and precise manner.

It is thus clear that the handle 1 according to the present invention acts as a limiter of the maximum first torque that can be transmitted to a mechanical drive component able to be connected to the handle 1 itself.

Advantageously, the maximum value of the first torque that can be transmitted is predetermined in advance and, therefore, the handle 1 can be used effectively and safely by any operator.

Indeed, in the case in which an operator exerts a second torque on the ring nut 4 the value of which is greater than a predetermined threshold value, the second connection means 7 provide for kinematically disconnecting the ring nut 4 from the support means 5.

With reference to the case in which the handle 1 is applied to a mechanical drive component of a fluid delivery device, the possibility of limiting the first torque that is transmitted to the component itself advantageously translates into the possibility of limiting the pressure and the speed with which such a fluid is delivered to a desired value.

In this way, potentially dangerous situations are avoided in which the fluid is delivered at a substantially higher pressure or speed with respect to maximum acceptable values, with reference for example to the case in which the fluid to be delivered is injected inside the human body.

Moreover, the handle 1 makes it possible to avoid possible bursting of the delivery device.

Concerning this, the maximum value of the first torque that can be transmitted by the handle 1 is established also as a function of the resistance of the delivery device.

The handle 1 makes it possible to avoid that inside the delivery device operatively connected to the same high pressures such as to determine the structural yielding of the delivery device to be reached.

This is particularly advantageous in the case of delivery of bone cement, with reference to what is described above.

According to an aspect of the present invention, the disengagement between the ring nut 4 and the support means 5 can be advantageously accompanied by a clicking, thus indicating that the second torque applied to the ring nut 4 is greater than a predetermined threshold value.

The clicking is produced by the at least one elastic element 16 knocking against the engagement means 17.

The operation of the handle 1 according to the invention is, in light of what is described, totally intuitive.

After having connected a handle 1 to a screw-type mechanical drive member, through the first connection means 3, the ring nut 4 is then made to rotate around the axis of rotation 6 by a second torque.

The ring nut 4 transmits the second torque to the support means 5 and, therefore, to the connection means 3.

As long as the value of the second torque applied to the ring nut 4 is less than or equal to a predetermined threshold value, the second connection means 7 keep the ring nut 4 kinematically connected to the support means 5.

At the moment when the value of the second torque exceeds a predetermined limit value, the second connection means 7 kinematically disconnect the ring nut 4 from the support means 5, thus interrupting the transfer of the first torque to the mechanical drive component.

In practice, at the moment when the value of the second torque exceeds a predetermined threshold value, the protuberances 21 of the second connection means 7 that act by thrusting against the free end 20 of the at least one appendage 19, deform the at least one elastic element 16 until the free end 20 is disconnected from the engagement means 17, thus allowing the relative sliding between the ring nut 4 and the support means 5.

As soon as the value of the second torque falls within a predetermined range of values, the at least one appendage 19 takes the respective free end 21 back firmly in abutment against a protuberance 21 of the engagement means 17, pulling in rotation the at least one elastic element 16 that in turn causes again the rotation of the support means 5 to which it is constrained.

Also an object of the present invention is a delivery unit 25 of a fluid, if so desired a liquid or a mixture, comprising a mechanical drive member 26 operatively connected to the aforementioned handle 1 through the first connection means 3 thereof.

Preferably, the delivery unit 25 comprises a container 27 delimiting a first chamber 28 inside which the fluid to be delivered is arranged, which can be removably connected, according to ways known in the field, to a handgrip 29 foreseen to be able to handle the delivery unit 25 itself.

The fluid to be delivered can for example be bone cement.

Figure 5:
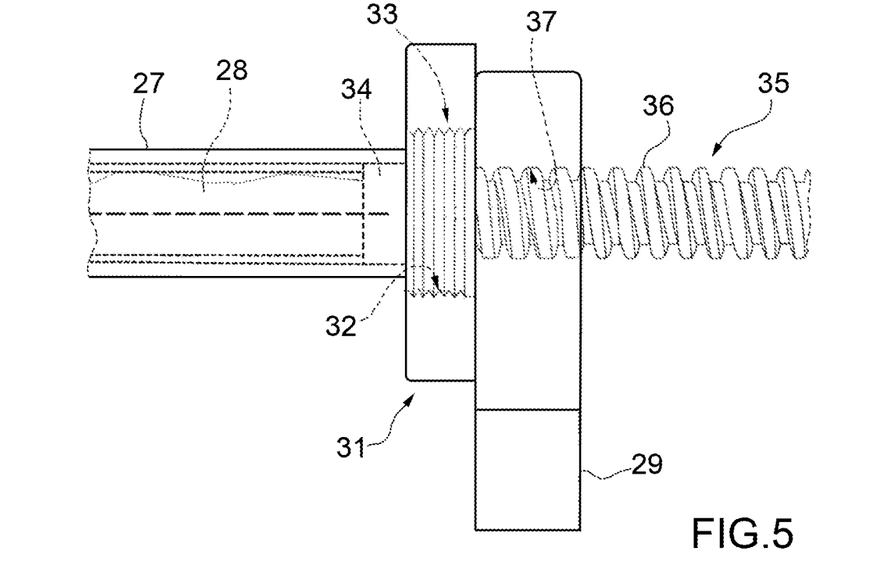
FIG. 5 is a side view of a detail in section of the delivery unit according to FIG. 3.

With reference to the embodiment illustrated in FIG. 5, the container 27, at a first end, has a supply channel 30 for the fluid to be delivered to come out from the first chamber 28, and at the opposite end to the first fastening means 31 to the handgrip 29 consisting of a portion 32 equipped with an internal threading intended to engage with an externally threaded tang 33 extending from the handgrip 29 itself.

However, the scope of protection of the present invention encompasses different fastening means 31 with respect to those described above suitable for allowing a removable connection between the container 27 and the handgrip 29, for example of the interlocking, bayonet or equivalent type.

Inside the chamber 28, a first piston 34, driven in translation through the mechanical drive member 26, is slidably engaged, forming a hermetic seal. Concerning this, the mechanical drive member 26 comprises a screw mechanism 35 the external threading 36 of which engages in an internal threading 37 made inside the handgrip 29, so as to advance following a rotation given to the screw 35 itself.

An end of the screw 35 is foreseen to press, in use, on the first piston 34, forcing it to slide along the first chamber 28, whereas the opposite end is operatively connected to the first connection means 3 of the handle 1.

In fact, the handle 1 controls the translation of the first piston 34 along the first chamber 28 pushing against fluid contained inside it.

According to an aspect of the present invention, by manually actuating the ring nut 4 in rotation around the axis of rotation 6 the screw mechanism 35 is caused.

In turn, the screw mechanism 35 causes the roto-translation of the first piston 34 along the first chamber 28.

At the moment when the value of the torque transmitted exceeds a predetermined threshold value, the second connection means 7, according to ways described earlier, disconnect the ring nut 4 from the support means 5, actually preventing the further advancing of the screw 35 along the chamber 28.

Usefully, in a delivery unit 25 according to the present invention it is possible to set the delivery conditions of the fluid as well as to limit the maximum pressure that can be reached inside the delivery unit 25.

Advantageously, by being able to establish the maximum torque that can be transmitted through the handle 1 to the mechanical drive member 26 it is possible to avoid, during the delivery of a fluid, undesired pressure spikes of the fluid delivered or inside the delivery unit itself, within a solution that is simple and easy to use as a whole.

Also an object of the present invention is a fluid delivery device 38, if so desired for a liquid or a mixture, of the type that can be actuated remotely. The remote activation of the delivery device 38 makes it possible to substantially reduce the exposure of an operator to contaminating agents, like for example radiation, present in the area in which it must operate.

Figure 6:
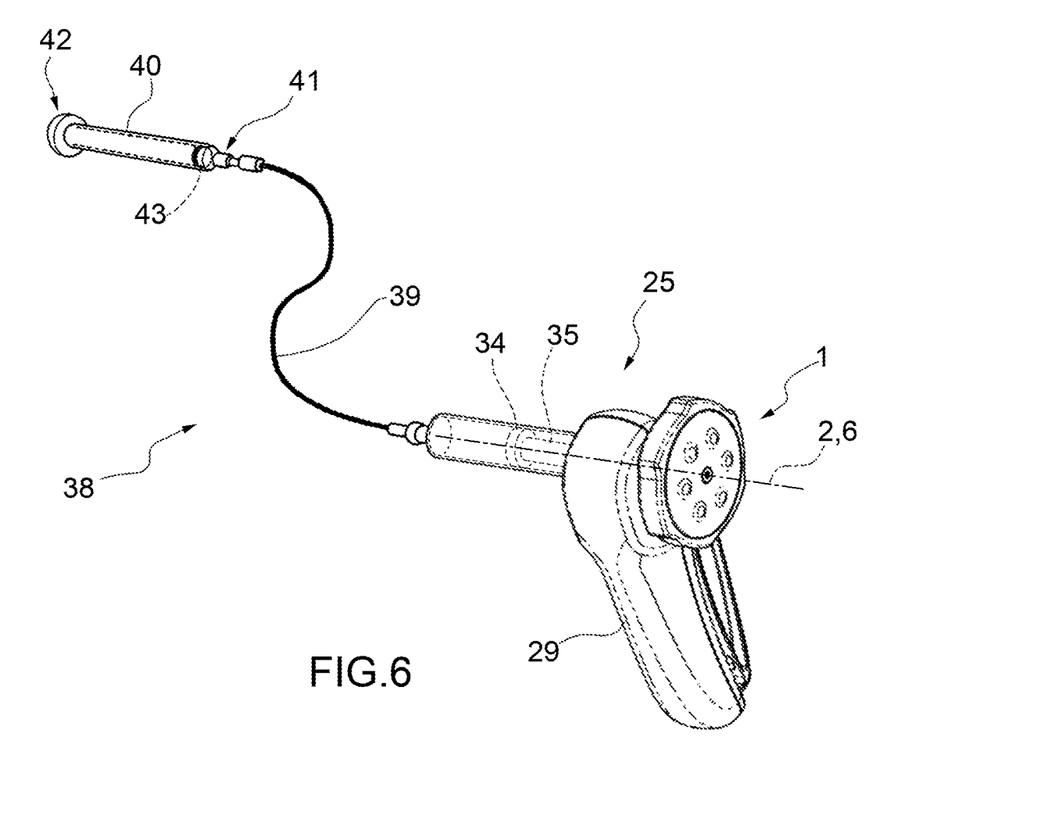
FIG. 6 is a schematic perspective view of a delivery unit according to FIG. 3 in a further embodiment.

With reference to the embodiment illustrated as an example and not for limiting purposes in FIG. 6, a delivery device 38 according to the present invention comprises a delivery unit 25 in fluid connection through a duct 39, to a syringe element 40, suitable for delivering a fluid, for example to be injected into the body of a patient.

Preferably, the syringe element 40 internally delimits a volume for containing a fluid to be delivered, according to ways known in the field.

The syringe element 40, at a first end, has a tang 41, possibly threaded, to which it is possible to connect an end of the duct 39 also advantageously equipped with a threaded portion.

The syringe element 40, at an end opposite the first end to which the duct 39 is connected, has a mouth 42, possibly threaded, for example for the connection to fluid delivery means such as a needle or similar, not illustrated in the figures.

Inside the syringe element 40, similarly to what has been described earlier for the container 27, there is a second piston 43 able to slide in a hermetically sealed manner.

A delivery unit 25 is operatively connected, in fluid communication through the duct 39 to the syringe element 40.

The delivery unit 25 acts as a pumping unit of a thrusting fluid for the second piston 43, suitable for making the latter translate inside the syringe element 40 and, consequently, for causing the fluid contained there to come out.

In practice, by acting on the handle 1 of the delivery unit 25 the thrusting fluid, contained in the container 27, is pumped through the duct 39 and then against the second piston 43 of the syringe element 40 causing the translation thereof.

Similarly to what was described for the delivery unit 25, the use of a handle 1 in a delivery device 38 makes it possible to limit the maximum pressure with which a fluid is delivered.

The present delivery device 38 also allows the advantages described earlier for the delivery unit 25 to be obtained.

The invention thus conceived can undergo numerous modifications and variants, all of which are covered by the inventive concept.

Moreover, all of the details can be replaced by other technically equivalent elements. In practice, the materials used, as well as the contingent shapes and sizes, can be whatever according to the requirements without for this reason departing from the scope of protection of the following claims.

The invention claimed is:
1. A handle connectable to a screw-type mechanical drive component for transmitting to the screw-type mechanical drive component a first torque, said handle comprising:

a first connector defining an axis for connection and constraint of said handle to said mechanical drive component, said first connector further comprising:

a ring nut to which a second torque is manually applicable, support means of said ring nut for rotationally supporting said ring nut around an axis of rotation coinciding, in use, with said constraint axis, said support means substantially shaped as a spool and comprising a first end portion, a second end portion and removable means for connecting said first end portion to said second end portion, and at least one elastic element comprising at least one appendage having an end, said at least one appendage deformable in a transverse direction for connecting/disconnecting said ring nut and said support means in a mechanically selective way so that said ring nut is kinematically connected to said support means when rotated in at least one rotation direction around said axis of rotation when said second torque is lower than a threshold value, and wherein said ring nut is kinematically disconnected from the support means when said second torque exceeds said threshold value, wherein said ring nut comprises an internal surface comprising at least one protuberance along said internal surface configured to intercept the end of the at least one appendage, an external surface separated from said internal surface, and lateral surfaces opposed to one another for connecting said internal surface and said external surface, said lateral surfaces each comprising a substantially annular shaped seat, wherein each of said first end portion and second end portion are laterally engaged to respective substantially annular shaped seats of said ring nut, and wherein said ring nut is kinematically disconnected from the support means by deformation of the at least one appendage of the elastic element in the transverse direction such that the end of the at least one appendage is disengaged from the at least one protuberance of the ring nut.

2. The handle according to claim 1, wherein said ring nut externally comprises at least one gripping element extending from said ring nut for facilitating gripping of said ring nut and the rotational actuation of said ring nut around said axis of rotation.

3. The handle according to claim 1, wherein said first end portion and said second end portion of said support means are substantially cylindrical or discoid shaped.

4. The handle according to claim 1, wherein said at least one elastic element is interposed, in use, between said ring nut and said support means.

5. The handle according to claim 4, wherein said at least one protuberance comprises a plurality of protuberances arranged substantially equidistant from one another.

6. The handle according to claim 1, wherein said at least one elastic element comprises a base portion from which said at least one appendage extends, said end of said at least one appendage being a free end engageable with said at least one protuberance substantially through shape coupling.

7. The handle according to claim 6, wherein said at least one appendage is substantially shaped like a curved blade.

8. The handle according to claim 1, wherein said at least one elastic element is removably connected to said support means or to said ring nut, while said at least one protuberance is positioned between said ring nut and said support means.

9. The handle according to claim 1, wherein said first connector include a seat centrally provided in said support means, said seat having a through-type opening passing through said support means for containing a screw or a connecting pin.

10. The handle according to claim 1, further comprising constraint means for preventing any relative rotation between the at least one elastic element and the support means.

11. The handle according to claim 1, wherein a fluid to be delivered is bone cement.

12. A delivery unit for a fluid, said delivery unit comprising: the handle of claim 1, a container, a coupling connecting said container to said handle, said container defining a chamber for containing said fluid to be delivered, a piston slidingly engaged in a sealed manner inside said chamber, said chamber having at a first end a channel for delivery of said fluid and at an opposite end or a second end a port shut by said piston, a screw-type mechanical drive component for translation of said piston along said chamber.

13. The fluid delivery unit according to claim 12, wherein said screw-type mechanism is rotationally translatable around and along an axis substantially coinciding with said axis of rotation of said handle, wherein a first end of said screw-type mechanism is engageable in abutment and thrusting against said piston and an opposite or a second end of said screw-type mechanism is constrained by said first connector of said handle.

14. A fluid delivery system for a fluid, said fluid delivery system comprising:

a syringe element inside which a second chamber is defined for containment of said fluid to be delivered, at least one second piston slidingly engaged in a sealed manner inside said second chamber of said syringe element, said syringe element showing at one end an outlet for delivery of said fluid and at an opposite end a tang, said fluid delivery system further comprising the fluid delivery unit of claim 12 in fluid connection with said syringe element.

* * * * *